(12) United States Patent
Lozano

(10) Patent No.: US 10,450,181 B2
(45) Date of Patent: Oct. 22, 2019

(54) SIMULATOR SYSTEM FOR DIFFERENT LIQUID FLAVORS

(71) Applicant: Alberto Adarve Lozano, Madrid (ES)

(72) Inventor: Alberto Adarve Lozano, Madrid (ES)

( * ) Notice: Subject to any disclaimer, the term of this patent is extended or adjusted under 35 U.S.C. 154(b) by 0 days.

(21) Appl. No.: 15/301,465

(22) PCT Filed: Mar. 31, 2015

(86) PCT No.: PCT/ES2015/070257
§ 371 (c)(1),
(2) Date: Oct. 3, 2016

(87) PCT Pub. No.: WO2015/150613
PCT Pub. Date: Oct. 8, 2015

(65) Prior Publication Data
US 2017/0121166 A1    May 4, 2017

(30) Foreign Application Priority Data
Apr. 4, 2014    (ES) .................................. 201400289

(51) Int. Cl.
| | | |
|---|---|---|
| *A61N 1/05* | (2006.01) | |
| *B67D 1/00* | (2006.01) | |
| *A61N 1/36* | (2006.01) | |
| *A61B 5/00* | (2006.01) | |

(52) U.S. Cl.
CPC ......... *B67D 1/0066* (2013.01); *A61N 1/0548* (2013.01); *A61N 1/36014* (2013.01); *B67D 1/0021* (2013.01); *A61B 5/4017* (2013.01)

(58) Field of Classification Search
CPC . A61N 1/36014; A61N 1/0548; A61B 5/4017
See application file for complete search history.

(56) References Cited

U.S. PATENT DOCUMENTS

| | | | |
|---|---|---|---|
| 2008/0234604 A1 | 9/2008 | Burgmans | |
| 2015/0283384 A1* | 10/2015 | Williams | ................ A61F 7/007 607/3 |
| 2017/0196495 A1* | 7/2017 | Yang | .................... A61B 5/4017 |

OTHER PUBLICATIONS

Nimesha Ranasinghe, Ryohei Nakatsu, Nii Hideaki, and Ponnampalam Gopalakrishnakone, "Tongue Mounted Interface for Digitally Actuating the Sense of Taste," in Proceedings of the 16th IEEE International Symposium on Wearable Computers (ISWC), Jun. 2012, pp. 80-87.*

(Continued)

*Primary Examiner* — Tammie K Marlen
(74) *Attorney, Agent, or Firm* — Larson & Larson, P.A.; Justin P. Miller; Frank Liebenow

(57) ABSTRACT

A system for achieving the sensation of drinking a particular drink, known as the target liquid, when in fact another drink, such as water, is being consumed. The system consists of a glass which contains not only water but also a small amount of the target liquid, in order to provide the true smell and image of the desired drink, as well as an electronic system for generating a series of signals which, by means of electrodes, stimulate the user's tongue to act on a series of nerve cells and provide the brain with a signal as similar as possible to that which the real drink provides to the taste buds of the user. The user of the system thus has the sensation of drinking the target liquid.

8 Claims, 1 Drawing Sheet

(56) References Cited

OTHER PUBLICATIONS

Nimesha Ranasinghe, Kuan-Yi Lee, and Ellen Yi-Luen Do, "Fun-Rasa: an interactive drinking platform," In Proceedings of the 8th International Conference on Tangible, Embedded and Embodied Interaction (TEI '14), ACM, 2014, pp. 133-136.*

Ranasinghe Net al. Tongue mounted interface for digitally actuating the sense of taste. 16th Annual International Symposium on Wearable Computers (ISWC), 2012, pp. 80-87, ISBN 978-I-4673-1583-8,<DOI: 10.1109/ISWC.2012.16>.

Ranasinghe, Net al. FunRasa. 8th International Conference on Tangible, Embedded and Embodied Interaction (TEI'I4), ACM, Feb. 16, 2014-Feb. 19, 2014, pp. 133-136, ISBN 978-1-4503-2635-3; ISBN 1-4503-2635-8, <DOI: 10.1145/2540930.2540939>.

* cited by examiner

SIMULATOR SYSTEM FOR DIFFERENT LIQUID FLAVORS

OBJECT OF THE INVENTION

The present invention relates to a simulator system for different liquid flavors, and more specifically to a system that simulates liquids with different flavors from a small quantity of the target liquid and water.

An object of the invention is to provide a system which, once a liquid (drink) is selected, which will be called a "target drink", and in conjunction with suitable programming, allows the user to drink a liquid, such as water, but achieve the sensation of enjoying the target drink, the sensation including the following characteristics:

1.—A flavor similar to that of the target liquid.
2.—A texture similar to that of the target liquid.
3.—A smell similar to that of the target liquid.
4.—A color similar to that of the target liquid.
5.—At a temperature to emphasize the previous characteristics.

FIELD OF APPLICATION OF THE INVENTION

The field of the invention is related to drink consumption.
A first classification of the drinks could be as follows:
Water
Health drinks
Infusions
Soft drinks
Other drinks Within infusions are included milk, chocolate, etc., in addition to tea, chamomile tea, linden tea, and similar.

Soft drinks include those that are ingested to quench thirst and have a sweet flavor.

Further included are wine and other alcoholic drinks, carbonated or non-carbonated. Alcoholic drinks provide certain beneficial properties if they are administered suitably and in very limited quantity.

For the purposes of the present invention, the drinks are initially classified in two large groups: carbonated and non-carbonated, and although a generalization thereof allows a much wider field, the invention is centered on those with a density similar to the density of water.

The object of the invention is to replace a drink, which we will call "target," with another, such as water, without the user being able to observe a difference between the water being consumed and the sensation of drinking the target drink. In addition, the invention may also be applied to avoid the unpleasant flavor of some drinks, such as, for example, a medicine that must be ingested.

In summary, if one can replace the entire set of drinks that are consumed for their flavor, together which those which are harmful for the subject, with simple water, the effect would be beneficial for health.

BACKGROUND OF THE INVENTION

There are few references of artificial flavor creation devices by means of electronic stimulation of the tongue's nerve cells.

Devices are known to generate flavor in artificial cigarettes, such as those disclosed in U.S. Pat. No. 6,125,853A and EP0845220B1, although in no case can they be considered a reference worthy of analysis or comparable with the object of the present invention.

DESCRIPTION OF THE INVENTION

The system of the invention provides the sensation by the corresponding means of stimulation, with drinking a liquid which we will call "target", of a similar density to what is being really drunk, "base liquid", and which will generally be carbonated or non-carbonated water.

The system claimed is capable of simulating the flavor of the target liquid by means of the electrical stimulation of different parts of the user's tongue, by means of a matrix of electrodes for said purpose. Likewise, it is capable of simulating the texture thereof, by means of the presence or absence of carbon dioxide in the water used.

As regards replicating the smell and the image, this is carried out by a small sample of the real target liquid.

Thus, for the smell and the image of the target liquid, a small sample of the target liquid is introduced into a small reservoir, in the part of the system corresponding to the nose, which is detailed below. In this way, the smell, the color, etc., of the real liquid are provided with absolute fidelity to the user.

The user will see and smell this small portion of target liquid, providing him or her with real sensations of the that desired smell and image.

The temperature is also modified with the system, with the aim of helping the appearance of the target liquid to be as close as possible to the real appearance.

The system consists of a vessel that is provided in correspondence with the lower part of its upper opening disposed for use, an element which adapts to the user's tongue, and which provides a series of stimuli with a matrix of electrodes placed inside it and which generates the electric patterns that simulate the stimulus in the way that the target liquid would generate in the neurons that lie behind the taste buds found in the user's tongue. This process stimulates the nerve cells, producing a similar effect to that which the real target liquid would generate.

The electronics generated by said stimulation are preferably located in two modules, one outside the vessel or container and another in the interior thereof, although all modules can be included within the container.

The electronics are comprised of a set of voltage/current generators.

Each generator consists of a function generator—a simple digital-analogue converter—and an amplifier. The quantity of generators matches the number of electrodes in the exciter element of the tongue. In a preferred form, the quantity is sixty-four, with greater quantities of electrodes able to create a closer match between the simulated flavor and the true sensation of the target liquid.

Aside from the mentioned generators, we should highlight the existence of a processor or microcontroller that generates the data that forms the stimuli signals, as well as other auxiliary functions, such as the detection and measurement of temperatures from temperature sensors for liquid, a temperature which will be suitable for said processor by means of the corresponding heating/cooling means, which can be materialized in simple electrical resistances or Peltier cells, to generate the desired temperatures. This processor will be provided with a data input to modify the behavior program which gives rise to the set of different stimuli for each target drink or flavor intended.

Of the Peltier cells, one generates the suitable temperature of the tongue according to the chosen target and helps in the system to obtain the selected stimuli. The other Peltier cell modifies the temperature of the base liquid to best adapt it to the intended effect.

In the upper part of the vessel, right in that area wherein the user's nose enters when he or she is drinking the liquid inside, a small reservoir is disposed, wherein a sample or small quantity of the target liquid is introduced with the aim of achieving an identical smell to the intended one, so that the user whilst drinking the water from the lower part of the vessel can see and smell the target liquid of the upper part thereof.

The vessel will mainly contain water, carbonated or non-carbonated, in accordance with the nature of the target liquid.

In a preferred form, the system is connected by means of a cable, via a plug, to externally powered electronics. The external power supply provides, while the electronics supplies the system with the appropriate signals for stimulation of the user's tongue.

In an alternative embodiment, the electronics are within the vessel, as well as a rechargeable battery or similar, which will allow storing energy for an autonomous operation, i.e. without connection with the cable, during a sufficient time for the use of the system.

The power supply can connect to the system by means of electromagnetic waves to avoid any physical connection of the system with the exterior. The same mechanism can be used to program the system with a new target liquid or flavor.

The tongue has taste buds or sensors mainly in the upper part. These sensors are responsible for the different ranges of tastes. The main objective of this invention is to be able to stimulate said sensors by means of electric means, generating a potential that excites them or by an electromagnetic process, similar to the previous but using a magnetic field to excite the nerve endings behind the taste buds in the user's tongue.

For the purposes described in the previous paragraph, the system has a matrix of electric or electromagnetic electrodes placed similarly to the tongue's sensors and which can be controlled independently by the previously specified electronics, by means of the use of the microcontroller and a sufficient number of output ports. Said processor will be associated with a control software which will be responsible for the uploading in memory of the desired patterns, as well as the generation of signals in accordance with it, which will be those responsible for generating the appropriate stimulation. At least one point or electrode provides the voltage reference to said generated circuits. In this preferred implementation, two points of mass or reference are used and an earth connection to avoid undesired currents in the user's body.

It also includes a sensor of inclination of the vessel which allows the system to start generating stimuli or stopping it, with the aim of saving energy when the system is in vertical position.

In short, it is a system whereby it aims to have the sensation of drinking the target liquid, when in fact what he or she is drinking is water or in certain special cases another base liquid.

Evidently, the advantages of drinking water instead of beer, wine, champagne or other soft drinks, whilst you think you are drinking said drinks, seem obvious and at least very advantageous in certain circumstances.

DESCRIPTION OF THE DRAWINGS

To complement the description that will be made below and in order to aid towards a better understanding of the characteristics of the invention, in accordance with a preferred example of practical embodiment thereof, a set of drawings is attached as an integral part of said description wherein, with illustrative and non-limiting character, the following has been represented.

PREFERRED EMBODIMENT OF THE INVENTION

Figure 1:
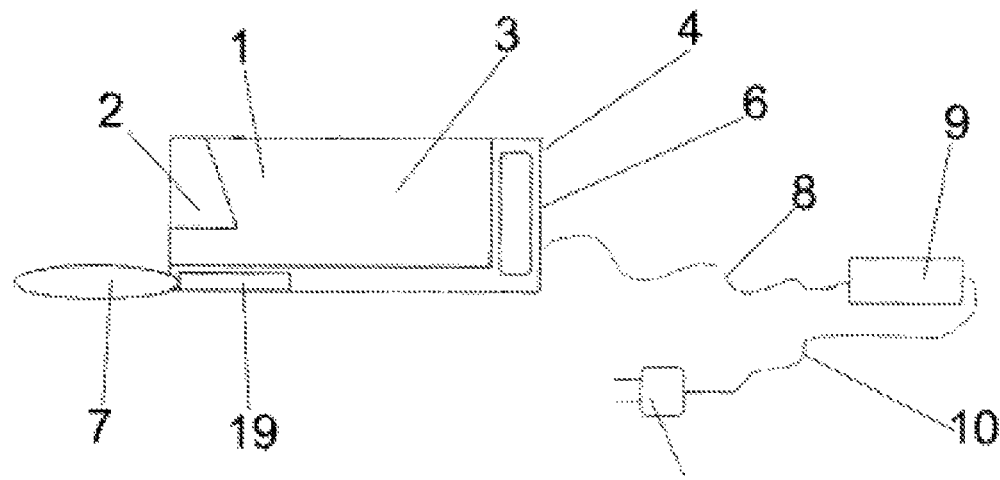
FIG. 1.—Shows the diagram corresponding to the system in which the system of the invention is materialized.

As can be seen in the mentioned figures, the device in which the system of the invention is materialized is formed from a container or vessel (1), with a reservoir (2) wherein a small quantity of target liquid is introduced, with the purposes of simulating the smell, and the vessel (1) whereof also includes a receptacle (4) where the control electronics (6) is placed, with the vessel (1) also including a main receptacle (3) wherein water is deposited which may be carbonated or non-carbonated, depending on the texture of the target liquid, so that in this main receptacle (3) it is possible to optionally include an additional Peltier or similar device to change the temperature of the liquid to ingest.

The vessel (1) is connected by means of a cable (8) to a voltage adapter (9) which is also connected to the mains by a plug (11) with its cable (10), although optionally all the electronics could be included in the vessel, assisted by the corresponding charger.

Figure 2:
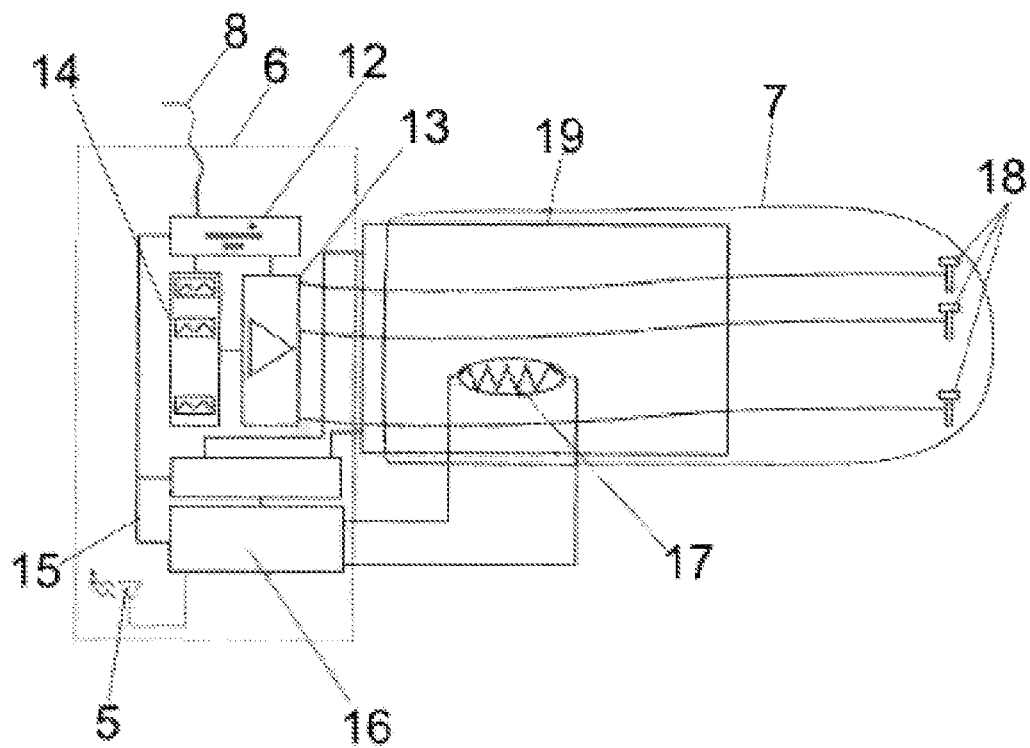
FIG. 2.—Shows the diagram corresponding to the electronics that participates in the device or system of the invention, as well as the Peltier cell and the support with the electrodes which also participate in the system or device of the invention.

FIG. 2 shows how the electronics (6) comprises a power supply (12), signal generators (14) with their respective amplifiers (13) which carry the amplified signal to electrodes (18) embedded in a support element (7), under which is located a Peltier cell responsible for regulating the temperature which is measured by a sensor (17), which carries the value measured to a processor (16) responsible for feeding back the energy provided to said Peltier (19) by a H bridge (15) or similar.

The programming of the processor (16) so that the desired stimuli are generated in the indicated electrodes (18), is performed from the exterior by electromagnetic waves, by means of a standard process such as that used in RFIDs, bluetooth, wi-fi, or more specifically by radio, which is provided with an antenna (5).

The system may also include an internal battery with its corresponding charger which will allow drinking without the need for the vessel to be joined with a cable to an external power source, as previously commented, and the internal battery of which is rechargeable to be able to continue supplying electricity to the system when it is not connected to an external charger, which may be an electromagnetic charger that generates radiofrequency waves capable of supplying energy to a coil within the device and thus recharge its batteries or elements for this purpose.

The fact should also be highlighted that the information for the programming can be transmitted by radio as previously stated, and captured by a coil inside the device, responsible for providing said information to the internal processor responsible for generating the suitable stimuli and thus the target flavors.

The temperature sensor which can be positioned beside the heat generator, may be a resistance which provides heat to the liquid to obtain the most suitable temperature in accordance with the intended target liquid, said heat/cold generator may be a Peltier cell, which provides cold or heat to the liquid to obtain the most suitable temperature in accordance with the intended target liquid.

Furthermore, we can highlight the fact that the element wherein the electrodes are disposed is soft and is molded to the upper form of the user's tongue and with the electrodes being preferably of electromagnetic type, i.e. they do not need physical contact with the tongue to generate the necessary stimuli, or have areas similar to those of the taste buds in the tongue.

Finally, it should be stated that the system may include one or more sensors which allow determining if the user is drinking to generate the stimuli and, thus, be able to save energy in generation of the stimuli whilst knowing the operating status of the system, which shall be complemented with a switch to turn it off, and may be manual or automatic operation.

The invention claimed is:

1. A simulator system for different liquid flavors, for a user, the user having a nose and a tongue, the system comprising:
    a vessel including:
    a reservoir;
    a target liquid contained within the reservoir;
        the target liquid selected from the group of: water, health drinks, infusions, soft drinks, milk, chocolate, tea, chamomile tea, linden, wine, alcoholic drinks, medicine, beer, or champagne;
    the reservoir adjacent to the nose of the user during use of the system, thereby allowing the user to smell the target liquid;
    a main receptacle containing water; and
    a secondary receptacle provided with electronics assisted by a voltage adapter, the secondary receptacle additionally comprising:
        a set of signal generators and a set of amplifiers to amplify a signal generated, and a set of electrodes adapted to excite one or more areas of the tongue that are sensitive to flavors;
    a processor controlling the electronics;
        the processor configured to control the electronics, generate an appropriate stimuli, and control an overall operation of the simulator system; and
    a support for the set of electrodes wherein when a user drinks, the water from the main receptacle comes into contact with the tongue of the user, causing the electrodes to make contact with the sensitive areas of the tongue.

2. The simulator system for different liquid flavors of claim 1, wherein the processor receives data for control and programming, the data received by a radio.

3. The simulator system for different liquid flavors of claim 1, further comprising:
    a Peltier cell with a temperature sensor;
    the Peltier cell acting to change a temperature of the water;
    the temperature sensor reporting a value representing the temperature of the water to the processor, the processor adjusting the Peltier cell to cause the temperature of the water to match a desired temperature.

4. The simulator system for different liquid flavors of claim 1, further comprising a temperature sensor together with a heat generator.

5. The simulator system for different liquid flavors of claim 1, wherein the electrodes are disposed in a soft element adapted to fit an upper form of the user's tongue.

6. The simulator system for different liquid flavors of claim 1, wherein the electrodes are of electromagnetic type.

7. The simulator system for different liquid flavors of claim 1, wherein the electrodes are distributed according to a natural distribution of taste buds on the user's tongue.

8. The simulator system for different liquid flavors of claim 1, further comprising a switch for switching off the simulator system, the switch being manual or automatic.

* * * * *